(12) United States Patent
Nickol et al.

(10) Patent No.: US 8,671,944 B2
(45) Date of Patent: Mar. 18, 2014

(54) SURFACE STRUCTURE ON PATIENT INTERFACE

(71) Applicant: ResMed R&D Germany GmbH, Martinsried (DE)

(72) Inventors: Johannes Nickol, Munich (DE); Adel Nibu, Munich (DE); Johann S. Burz, Germaringen (DE); Achim Biener, Aufkirchen (DE); Bernd Lang, Grafelfing (DE)

(73) Assignee: Resmed R&D Germany GmbH, Martinsried (DE)

( * ) Notice: Subject to any disclaimer, the term of this patent is extended or adjusted under 35 U.S.C. 154(b) by 0 days.

(21) Appl. No.: 13/783,008

(22) Filed: Mar. 1, 2013

(65) Prior Publication Data

US 2013/0174851 A1 Jul. 11, 2013

Related U.S. Application Data

(63) Continuation of application No. 12/461,026, filed on Jul. 29, 2009, now Pat. No. 8,397,729.

(30) Foreign Application Priority Data

Jul. 29, 2009 (EP) .................................. 09166681

(51) Int. Cl.
*A62B 18/08* (2006.01)

(52) U.S. Cl.
USPC ............. 128/206.24; 128/206.28; 128/207.13

(58) Field of Classification Search
USPC ............. 128/205.25, 206.12, 206.23–206.28, 128/207.13
See application file for complete search history.

(56) References Cited

U.S. PATENT DOCUMENTS

| 6,408,853 | B1 | 6/2002 | Chang |
| 8,397,729 | B2 | 3/2013 | Nickol et al. |
| 2008/0041388 | A1 | 2/2008 | McAuley et al. |

FOREIGN PATENT DOCUMENTS

| DE | 10 2005 042 182 | 10/2006 |
| WO | 2004/108048 | 12/2004 |
| WO | 2005/053781 | 6/2005 |
| WO | 2009/062265 | 5/2009 |

OTHER PUBLICATIONS

Search Report for corresponding European Application No. 09 16 6681.8, 5 pages.
Search Report for corresponding European Application No. 09 16 6681.8, 5 pages, Dec. 29, 2009.

*Primary Examiner* — Glenn Richman
(74) *Attorney, Agent, or Firm* — Nixon & Vanderhye, P.C.

(57) ABSTRACT

The present invention relates to the surface structure of a plastic material and particularly of silicone surfaces. More particularly, the present invention relates to the surface structure of the surfaces of a breathing mask assembly or a patient interface to be used for supplying breathing gas to a patient. Such patient interface for providing respiratory gas to a patient comprises a contact surface for contacting a patient's skin, wherein at least a part of said contact surface is a structured surface.

21 Claims, 3 Drawing Sheets

SURFACE STRUCTURE ON PATIENT INTERFACE

CROSS REFERENCE

This application is a continuation of U.S. patent application Ser. No. 12/461,026, filed Jul. 29, 2009, allowed, which claims priority to European Patent Application No. 09166681.8 filed Jul. 29, 2009, the entire contents of each of which are hereby incorporated by reference in this application.

BACKGROUND OF THE INVENTION

The present invention relates to the surface structure of a plastic material and particularly of silicone surfaces. More particularly, the present invention relates to the surface structure of the surfaces of a breathing mask assembly or a patient interface to be used for supplying breathing gas to a patient.

STATE OF THE ART

In the art, polished and rough or matt finished surfaces are known to be provided with breathing masks for providing breathing a respiratory gas to a patient. In particular, it is known to provide such surface textures, i.e., polished or matt finished surfaces, as contact surfaces between such breathing mask or patient interface and a patient.

Moreover, it is known to provide contact surfaces, e.g., at forehead pads supporting a breathing mask on the forehead of a patient, having a certain structure that prevents or counteracts the so-called sucking effect occurring when pressing a concave plastic or silicone surface on a patient's forehead. This is known, e.g., from the breathing masks sold under the trade name Papillon™ of ResMed GmbH & Co, KG, the forehead pads of which are provided with a small number of defined/symmetrical grooves that allow air to flow through these grooves between the forehead pad surface and the patient's skins thereby counteracting the sucking effect.

DE-A-100 45 183 refers to a forehead pad of a breathing mask which is provided with holes or channels in order to avoid the sucking effect of the forehead pad on a user's skin.

DE-A-102005042182 refers to a breathing device, wherein the air path of the breathing device is provided with a surface being optimised for air flow which enables a reduction of the coefficient of an air flow resistance. The various configurations of the surface are carried out in nanometer scale. The disclosed structures may be considered as polished surface. Notwithstanding the scale of the configuration of the surface and the different fields of application, the surface is not suitable for contacting with the patient's skin as the upper portions of the surface are substantially formed spiky like apexes.

DRAWBACKS OF THE PRIOR ART

The devices known in the prior art are disadvantageous in that their contact surfaces which are pressed onto a user's skin may lead to reddening or pressure marks of or on the user's skin and/or make the user feel uncomfortable.

OBJECT UNDERLYING THE INVENTION

It is an object underlying the present invention to overcome the problems of the prior art. In particular, it is an object to provide contact surfaces of a patient interface which are adapted to be in contact with the user's skin and which provide excellent functionality, particularly as regards, e.g., the support of the patient interface on the user's skin and/or the sealing of the mask interior, and which at the same time overcome the disadvantages of the prior art and particularly make the patient feel comfortable and/or which provide further functionalities.

SUBJECT-MATTER UNDERLYING THE INVENTION

The object underlying the present invention is achieved by the features of the independent claims wherein the dependent claims are directed to preferred embodiments of the present invention.

According to the present invention there is provided a contact surface, preferably a plastic contact surface and more preferably a silicone contact surface, of a patient interface such as a breathing mask, at least a part of which is a structured surface.

According to the present invention, a structured surface is not a polished surface and/or not a matt surface. According to the present invention a structured surface is understood to be a surface comprising a certain surface topography. Preferably, according to such preferred topography of a structured surface, up to about 90% of said structured surface lie over a first topography level and wherein at least about 10% of said structured surface lie below a second topography level. The first topography level preferably lies outwardly from the second level with regard to the structured surface and/or the second topography level is preferably recessed, depressed or set back with regard to the first level or the structured surface. A Topography level is understood to basically extend generally parallel to the surface but it may also be inclined or comprise changing inclinations.

Preferably, up to about 80% of the structured surface lie above or on the first surface level and at least about 20% lie below on the second surface level. More preferably, up to about 60-80 and most preferably about 70% of the surface lie above or on the first topography level and at least about 20-40% and preferably about 30% of the structured surface lie below or on the second topography level. According to a preferred embodiment, the structured surface comprises at least two, preferably a third or more topography levels, wherein the third or more topography level(s) lay between the first (or outer) and second (or inner) topography levels and wherein portions of the surface lay on these third and/or more topography levels.

Preferably, the first and second topography levels are spaced from one another (depth) by about 0.04 to 0.1 mm and/or 0.1 to 0.6 mm, more preferably by about 0.05 to 0.08 mm and/or less than 0.5 mm, or even more preferably by about 0.06 to 0.07 mm Preferably, the area of surface portions continuously lying over or on the first topography level lies in the range of about 50% to 95% of the overall surface area (i.e., surface area lying on and above the first surface level and on and below the second surface level) of the structured surface, preferably in the range of about 65% to 95% of the overall surface area, and more preferred in the range of about 75% to 90%.

According to a preferred embodiment, the structured surface comprises grooves, depressions, channels, cavities, ridges, notches, bulges, dents and/or the like. Preferably due to these shapes and particularly due to their height or depth a surface comprising such shapes becomes a structured surface. The distribution of the respective geometrical shapes as referred to above and by means of which the surface becomes a structured surface is preferably approximately regularly along the structured surface. However, the distribution of the respective shapes needs not to be symmetrical or regular but may also be asymmetrical or irregular.

Preferably, the distribution of the respective means or shapes along the structured surface is considered as being regular as long as preferably at lest about 0.5 cm², 1 cm² or 1.5 cm² of a structured surface fulfill the above definition for a structured surface.

Preferably, the structured surface comprises, particularly due to the provision of upper and lower topography levels, at least raised or upper surface portions of preferably one topography level and recessed or lower surface portions of preferably another topography level. There may further be additional surface portions lying between the upper and the lower portions.

Preferably, the surfaces of the raised or upper portions of the structured surface substantially lie in an envelope enveloping said structured surface. Such envelope preferably describes the surface the structured surface would have if it was a non-structured or polished surface. Preferably, the structured surface is a negatively structured surface. In other words, the structured surface can preferably be distinguished from a flat or plane surface in that is has a number of grooves, channels, depressions, cavities, notches, bulges and/or dents etc. vis-à-vis the surface of such flat or plane surface.

According to the present invention, a structured surface can be achieved by various shapes or topography forms, as indicated above, wherein also different shapes or topography forms may be mixed or used in combination in order to form a structured surface.

The present invention further relates to a patient interface comprising such structured contact surface for contacting a patient's skin and particularly comprising a silicone structured contact surface. More preferably, the patient interface comprises a pillow or cushion for sealingly contacting the user's skin around of a patient's mouth and/or nose wherein such contact surface comprises one or more structured surfaces or surface portions.

Preferably, at least about 30% of the contact surface area of a patient interface is a structured surface and more preferably more than about 50% or more than about 60% of the contact surface is a structured surface. Even more preferred, the whole contact surface or up to 90% or more and preferably up to about 70% of the contact surface of a patient interface are structured surface. The contact surface of a patient interface is understood to be the surface for contacting the patient's skin when the interface is worn by the patient.

The present invention provides, according to a preferred embodiment, a structured surface having a texture comparable to a natural texture or leather. Generally, such structured surface comprises a number of irregularly running grooves or narrow channels of different, changing and/or regular depths, widths etc. Between these grooves or narrow channels there arise raised surface portions or islands the surfaces of which are preferably substantially on the same level. Such texture provides a particularly improved haptic thereby achieving a less sticky, fresher feeling for the users being in contact with such surface. Preferably, the grooves or second topography level is distanced from the islands or first topography level by about 0.04 to 0.1 mm, more preferably by about 0.05 to 0.08 mm, or even more preferably by about 0.06 to 0.07 mm or up to about 0.1 mm. In other words, the depth of the grooves or the like vis-à-vis the raised surface portions are substantially within the above range.

The present invention provides, according to a preferred embodiment, a structured surface having a texture comparable to a lizard's or saurian's skin. Generally, such structured surface also comprises a number of irregularly running grooves or narrow channels of different, changing and/or regular depths, widths etc. Between these grooves or narrow channels there arise raised surface portions or islands the surfaces of which are preferably substantially on the same level. Preferably, the grooves or second topography level is distanced from the islands or first topography level by about 0.05 to 0.6 mm, more preferably by about 0.2 to 0.5 mm, or even more preferably by less than 0.8 mm. In other words, the depth of the grooves or the like vis-à-vis the raised surface portions are substantially within the above range. Such texture provides a particularly improved haptic thereby achieving a less sticky, fresher feeling for the users being in contact with such surface. Alternatively or additionally, such structured surface preferably provides or allows a vent-effect. In other words, the surface is structured so that a limited and controlled amount of air inside a face mask, particularly when the air inside the mask is pressurised compared to the ambient air, is allowed flow out of the mask, due to the topography of the structured surface, between the contact surface of the mask and the user's skin.

According to further preferred embodiments, particularly the above discussed structures, are provided having a scaled appearance, e.g. by providing a scale like shape of the raised surface portion and/or by providing the raised surface portions with an inclination. According to other preferred configurations, the depressed portions or channels are arranged radially and/or parallel to one another.

The present invention allows the provision of contact surfaces, particularly silicone contact surfaces, having, at least partially, a structured surface is particularly advantageous in that such structured surface (i) influences optic and design of the product, (ii) allows the provision of different haptic options, and (iii) allows new functionalities.

It has been found out that the provision of a structured surface according to the present invention positively influences optic and design of the product provided with such structured surface and particularly improves both the patient's subjectively felt quality of the product as well as the objective quality of the product.

Moreover, a structured surface according to the present invention improves the haptic qualities of the respective surface and thus the patient's comfort. In particular, plastic and particularly silicone surfaces having a polished appearance are generally sticky or considered as being sticky and when applied with pressure onto a patient's skin may lead to pressure marks or reddening of the patient's skin. Contrary thereto, a structured surface according to the present invention allows a certain degree of venting of the patient surface contacting the patient interface. For example, the structure can be considered to allow some contact between the patient's skin and air via the plurality of grooves, channels, depressions or the like. This preferably enables the perspiration of the patient's skin. The structured surface is not sticky but allows such structured surface to slide on a user's skin thereby still allowing the provision of a sealing contact between such structured surface and the user's skin. In particular, the structured surface according to the present invention is designed such that it prevents reddening and/or irritation of the patient's skin or marks to appear on the users skin. The structured surface also provides for a change of contact zones and pressure distribution once its position is—even if only slightly—changed. In order to avoid marks to appear on a users skin, it is preferred that the depressions or channels on the structured surface are not too deep.

The provision of structured surfaces according to the present invention allows the introduction of, e.g., ventilation channels or skin-vent structures as aforementioned. These preferably improve the comfort of the patient leading to, e.g., less sweating, allowing the skin to breath and/or to be cooled.

The present invention further relates to the use of a structured surface to contact a person's skin as well as to be used as a contact surface of a patient interface as well as to a method of production of such structured surfaces and to a tool formed for manufacturing structured surfaces and its production.

In the following, preferred embodiments underlying the present invention will be discussed in a non-limiting way by reference to the Figures of which:

FIG. 3 shows a top view onto a preferred schematic structured surface, wherein

Figure 1:
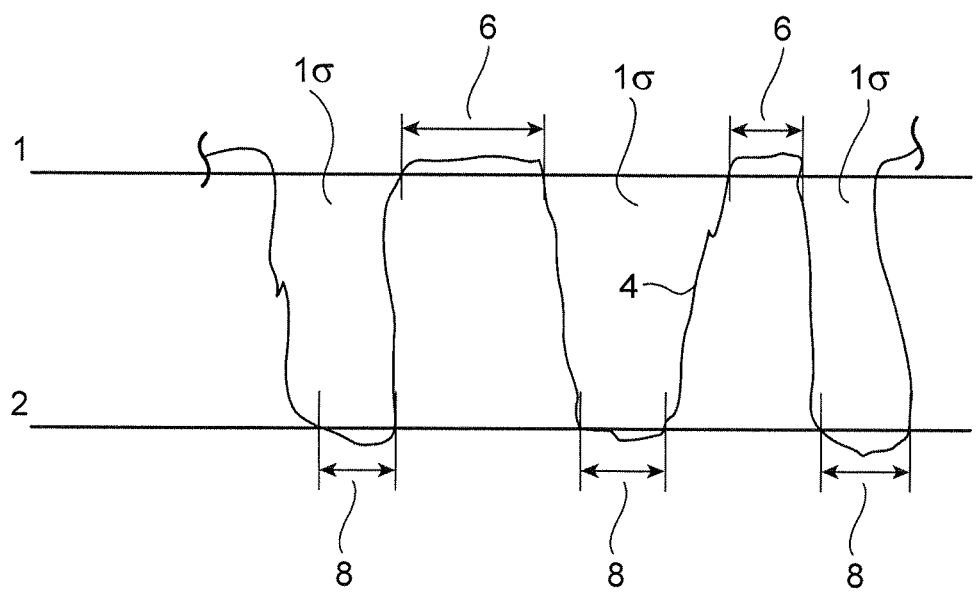
FIG. 1 shows a schematic cross section through a preferred structured surface according to the present invention.

FIG. 1 shows a schematic cross section through a preferred structured surface according to the present invention. Indicated is a first, upper, topography level 1 and a second, lower, topography level 2, wherein some portions 6 of the surface 4 shown lie on or above said first or upper topography level 1 and wherein some portions 8 of the surface 4, here at least parts of the bottom surfaces of the grooves 10 lie on or below a second, lower, topography level 2. The first and second topography levels are distanced from one another wherein the second topography level is recessed or set back with regard to the first topography level which is closer to the outside of the surface. As can bee seen in FIG. 1, the structured surface comprises a number of recesses, grooves or channels 10 or the like, which preferably extend between the upper and the lower or first and second topography level. Preferably, the bottom or parts of the bottom of said recesses or grooves 10 lay below or on or constitute the second topography level. The recesses or grooves 10 may be regular and/or irregular and their side surfaces may be straight, inclined, plane and/or irregular. According to the preferred embodiment as shown e.g. in FIG. 1 there is only a first and a second topography level. According to further preferred embodiments, there is/are provided one or more additional topography levels. These are preferably arranged between the first and second topography level and/or above and/or below the first and/or second topography level.

Figure 2:
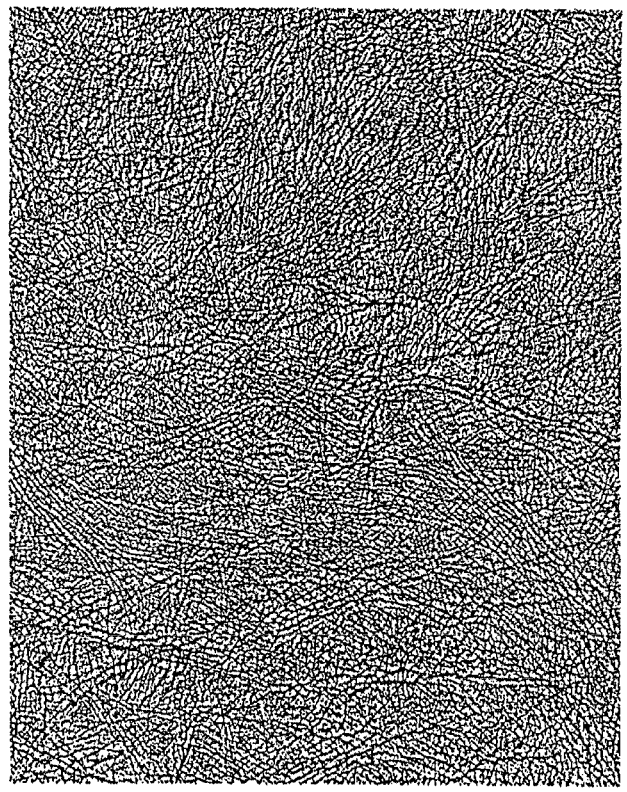
FIG. 2 shows a top view onto a preferred schematic structured surface.

FIG. 2 shows a structured surface 4 having a texture comparable to a natural texture or leather. The structured surface comprises a number of irregularly running grooves or narrow channels 10 of different, changing and/or regular depths, widths etc. Between these grooves or narrow channels there arise raised surface portions or islands 6 the surfaces of which are preferably substantially on the same level an on or above a first or upper topography level. In FIG. 2, the upper or raised portions 6 are indicated in bright(er) or white colour whereas the lower or recessed portions 4 of the grooves or channels are indicated in dark(er) or black colour. Preferably, the grooves 10 or surface portions 4 on or below the second topography level 2 are distanced from the islands or surface portions 6 on or above the first topography level 1 by about 0.04 to 0.1 mm, more preferably by about 0.05 to 0.08 mm, or even more preferably by about 0.06 to 0.07 mm or up to 0.1 mm. In other words, the depth of the grooves vis-à-vis the raised surface portions or the distance between the first 1 and second 2 topography level is substantially within the above range. Moreover, the ratio between the area of the surface portion 6 lying on or above the first topography level 1 and the surface portion 8 lying on or below the second topography level 2 is preferably about 9.5 to 0.5, 9 to 1, 8 to 2, 7 to 3 or 6 to 4.

Preferably, this ratio applies also or alternatively to the area or total area of the surface portions 6 lying on or above the first topography level 1 and the surface portions 8 lying on or below the second topography level 2. The width of the channels or grooves 10 is preferably in the range from about 0.01 to 1.2 mm, 0.05 to 0.8 mm, 0.09 to 0.6 mm or 0.1 to 0.4 mm.

This texture preferably provides a particularly improved haptic thereby achieving a less sticky, fresher feeling for the users being in contact with such surface.

Figure 3A:
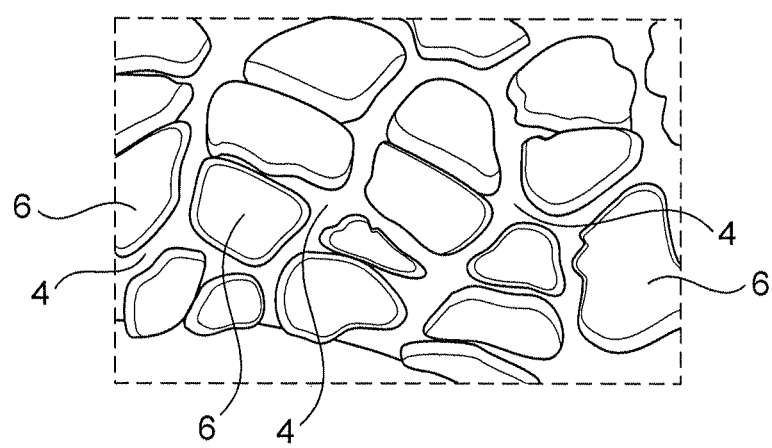
FIGS. 3a and 3b show different preferred schematic structures.
Figure 3B:
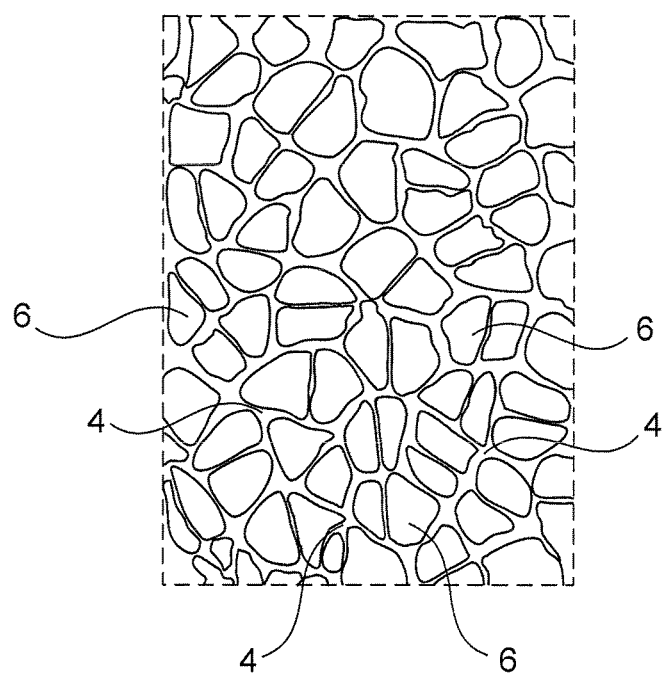

FIGS. 3a and 3b show a preferred structured surface 4 having a texture comparable e.g. to a lizard's or saurian's skin. Generally, as the structured surface shown in FIG. 1 such structured surface also comprises a number of irregularly running grooves or narrow channels 10 of different, changing and/or regular depths, widths etc. Between these grooves or narrow channels 10 there arise raised surface portions or islands 6 the surfaces of which are preferably substantially on the same level and on or above a first or upper topography level 1. Surface portions 8 of the grooves or channels 10, preferably the bottom surfaces of the grooves or channels 10 lie on or below a second or lower topography level 2. Preferably, the surface portions 8 and/or the second topography level 2 is distanced from the islands 6 and/or the first topography level 1 by about 0.1 to 0.6 mm, more preferably by about 0.2 to 0.5 mm, or even more preferably by less than 0.8 mm. In other words, the depth of the grooves or the like vis-à-vis the raised surface portions and/or the distance between the first 1 and second 2 topography level is substantially within the above range. Moreover, the ratio between the area of the surface portions 6 lying on or above the first topography level 1 and the surface portions 8 lying on or below the second topography level 2 is preferably about 9.5 to 0.5, 9 to 1, 8 to 2, 7 to 3 or 6 to 4. The width of the channels or grooves 10 is preferably in the range from about 0.1 to 1.2 mm, 0.2 to 0.8 mm, 0.3 to 0.6 mm or 0.4 to 0.5 mm.

The texture or surface structure according to the embodiment shown in FIG. 3 provides a particularly improved haptic thereby achieving a less sticky, fresher feeling for the users being in contact with such surface. Alternatively or additionally, such structured surface preferably provides or allows a vent-effect and is structured so that a limited and controlled amount of air inside a face mask, particularly when the air inside the mask is pressurised compared to the ambient air, is allowed flow out of the mask, due to the topography of the structured surface, between the contact surface of the mask and the user's skin. The grooves or channels 10 preferably allow pressurized air exit a face masks interior when the mask is being worn by user.

The negative or inverse structured surface in a tool for producing such structured surface in accordance with the present invention is preferably provided by an etching process or a process including etching.

It is understood that the different surface structures and embodiments as discussed above can be readily combined, either distinct or overlapping, e.g. in a product, such as a face mask cushion.

What is claimed is:

1. A patient interface to provide respiratory gas to a patient comprising a contact surface to contact a patient's skin, wherein at least a part of said contact surface is a structured ventilation surface, wherein the structured ventilation surface comprises contact surface portions to contact the skin of the patient and bottom surface portions separating the contact surface portions, said contact surface portions comprising a greater proportion of a surface area of the structured ventilation surface than the bottom surface portions.

2. A patient interface according to claim 1, wherein said patient interface is supported on a cushion.

3. A patient interface according to claim 1, wherein the contact surface lies on and/or above a first topography level and a bottom surface lies below and/or on a second topography level.

4. A patient interface according claim 3, wherein the first topography level is distanced from the second topography level, and wherein the first topography level lies outwardly from the second level with regard to the structured ventilation surface and/or the second topography level is depressed or inwardly set back with regard to the first topography level and/or the structured ventilation surface.

5. A patient interface according to claim 3, wherein the topography levels lie in substantially parallel planes.

6. A patient interface according to claim 3, wherein up to about 95% of said contact surface lie on and/or above the first topography level and wherein at least about 5% of said bottom surface lie on and/or below the second topography level.

7. A patient interface according to claim 3, wherein up to about 80% of the contact surface lie on and/or above the first topography level and at least about 20% of said bottom surface lie on and/or below the second topography level.

8. A patient interface according to claim 3, wherein up to about 60% to 80% of the contact surface lie on and/or above the first topography level and at least about 20% to 40% of the bottom surface lie on and/or below the second topography level.

9. A patient interface according to claim 3, wherein the first and second topography levels are spaced from one another by about 0.04 to 0.1 mm.

10. A patient interface according to claim 3, wherein the first topography level is distanced from the second topography level by less than 0.8 mm.

11. A patient interface according to claim 3, wherein the structured ventilation surface further comprises additional surface portions lying between the first topography level and the second topography level.

12. A patient interface according to claim 3, wherein the contact surface comprises the contact surface portions and the contact surface portions that lie on and/or above the first topography level are distanced from one another by about 0.1 to 1.2 mm.

13. A patient interface according to claim 12, wherein the contact surface portions that lie on and/or above the first topography level are distributed regularly across continuous areas of at least about 0.5 cm$^2$.

14. A patient interface according to claim 3, wherein the bottom surface comprises the bottom surface portions and the bottom surface portions lying below and/or on the second topography level are interconnected.

15. A patient interface according to claim 14, wherein the interconnected bottom surface portions lying below and/or on the second topography level are interconnected to allow gas inside the patient interface to flow out of the patient interface when the patient interface is worn.

16. A patient interface according to claim 1, wherein the contact surface and the bottom surface form a marbled, nerved, flaked or scaly structure.

17. A patient interface according to claim 1, wherein the patient interface is comprised of plastic or silicone.

18. A patient interface according to claim 1, wherein the contact surface portions comprises ridges, bulges, and/or bulbs.

19. A patient interface according to claim 1, wherein the structured ventilation surface is an irregular structured ventilation surface.

20. A patient interface according to claim 1, wherein the bottom surface portions comprises grooves, channels, depressions, cavities, notches, and/or dents.

21. A patient interface according to claim 1, wherein the contact surface portions are not uniform.

* * * * *